United States Patent [19]

Wojtowicz

[11] 4,055,719
[45] Oct. 25, 1977

[54] PROCESS FOR PRODUCING TRICHLOROISOCYANURIC ACID FROM SELECTED SYMMETRICAL TRIAZINES

[75] Inventor: John A. Wojtowicz, Chesire, Conn.

[73] Assignee: Olin Corporation, New Haven, Conn.

[21] Appl. No.: 699,825

[22] Filed: June 25, 1976

[51] Int. Cl.$^2$ .......................................... C07D 251/28
[52] U.S. Cl. ................................................... 544/190
[58] Field of Search ..................................... 260/248 C

[56] References Cited

U.S. PATENT DOCUMENTS

| | | | |
|---|---|---|---|
| 3,988,336 | 10/1976 | Wojtowicz | 260/248 |
| 3,993,649 | 11/1976 | Sawhill et al. | 260/248 |

Primary Examiner—John M. Ford
Attorney, Agent, or Firm—James B. Haglind; Donald F. Clements; Thomas P. O'Day

[57] ABSTRACT

Trichloroisocyanuric acid is produced by the reaction of a symmetrical triazine compound selected from the group consisting of ammelide, chlorosubstituted ammelide, ammeline and chlorosubstituted ammeline, with dichlorine monoxide in a gaseous mixture with a diluent gas. The gaseous mixture is comprised of from about 1 to about 30 percent by volume of dichlorine monoxide.

7 Claims, No Drawings

PROCESS FOR PRODUCING TRICHLOROISOCYANURIC ACID FROM SELECTED SYMMETRICAL TRIAZINES

This invention relates to a process for the production of trichloroisocyanuric acid from selected symmetrical triazine compounds. Trichloroisocyanuric acid is a commercial product used in washing, bleaching and sanitizing applications.

It is known to react chlorine gas with amides or imides of cyanuric acid such as ammelide or ammeline to produce chlorinated ammelide and chlorinated ammeline as described in U.S. Pat. No. 2,184,886, issued to Muskat et al. These chlorinated compounds, while containing considerable amounts of active chlorine, have found little use and are not produced commercially.

Now it has been found that symmetrical triazine compounds such as ammelide and ammeline can be converted to trichloroisocyanuric acid, a well known commercial product.

An object of the present invention is a process for preparing trichloroisocyanuric acid from selected symmetrical triazine compounds.

Another object of the present invention is a process for preparing trichloroisocyanuric acid from selected symmetrical triazine compounds which does not require use of a liquid solvent medium and a separate drying step.

A further object of the present invention is a process in which trichloroisocyanuric acid is obtained directly as a dry product.

These and other objects of the present invention will be apparent from the following detailed description of the invention.

Briefly, the process of the present invention for producing trichloroisocyanuric acid comprises reacting a symmetrical triazine compound selected from the group consisting of ammeline, chlorosubstituted ammeline, ammelide, chlorosubstituted ammelide, and mixtures thereof with a gaseous mixture containing chlorine monoxide and a diluent gas. The gaseous mixture is comprised of from about 1 to about 30 percent by volume of dichlorine monoxide.

More in detail, symmetrical triazine compounds such as ammelide or ammeline are known compounds which can be synthesized by known methods. Ammeline, is prepared for example, by the reaction of cyanoguanidine with urea, ammonia, or potassium cyanate while ammelide can be synthesized, for example, by the pressurized reaction of dicyandiamide with $CO_2$.

Both compounds also are often present as impurities in cyanuric acid which has been prepared by the pyrolysis of urea. In addition to ammeline and ammelide, chlorosubstituted derivatives such as dichloroammeline, monochloro- or trichloroammelide may be used in the process of the present invention.

Dichlorine monoxide is prepared by processes well known in the prior art, for example, by the reaction of chlorine gas with mercuric oxide according to the equation:

$$2Cl_2 + 2HgO \rightarrow Cl_2O + HgCl_2 \cdot HgO \qquad (1)$$

Another suitable method of preparation for dichlorine monoxide is the chlorination of sodium carbonate or sodium bicarbonate illustrated by the following equations:

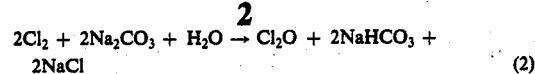

$$2Cl_2 + 2Na_2CO_3 + H_2O \rightarrow Cl_2O + 2NaHCO_3 + 2NaCl \qquad (2)$$

$$2Cl_2 + 2NaHCO_3 \rightarrow Cl_2O + 2CO_2 + H_2O + 2NaCl \qquad (3)$$

A detailed procedure for each of these methods of preparation for dichlorine monoxide is given in the publication Inorganic Synthesis, 5, 156–160, (N.Y. McGraw-Hill, 1957).

To eliminate potential explosion hazards the dichlorine monoxide is employed in a gaseous mixture with a diluent gas. Suitable diluent gases include air, nitrogen, carbon dioxide, chlorine, and nitrous oxide, with air, chlorine and nitrogen being preferred. The gaseous mixture suitably comprises from about 1 percent to about 30 percent by volume of dichlorine monoxide. Preferably, the gaseous mixture comprises from about 5 percent to about 25 percent and more preferably from about 10 percent to about 23 percent of dichlorine monoxide.

In the process of the present invention, ammelide and ammeline are believed to react with dichlorine monoxide to produce a reaction mixture containing trichloroisocyanuric acid according to the following equations:

(4)

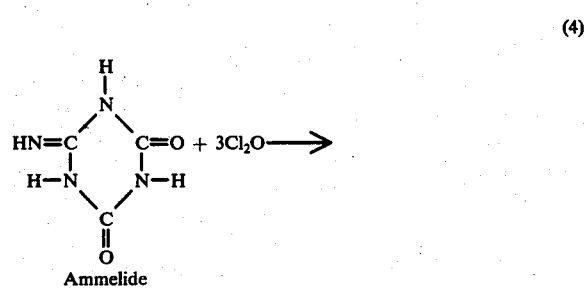

Ammelide

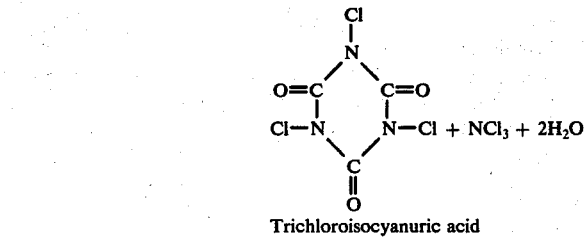

Trichloroisocyanuric acid (5)

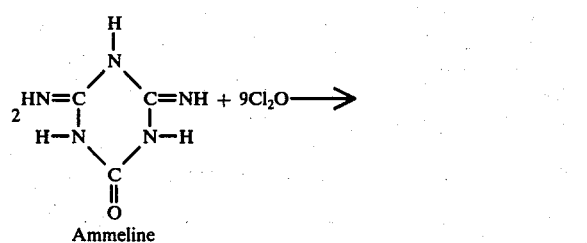

Ammeline

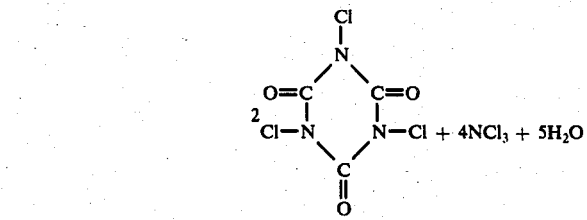

In the above equations, ammeline and ammelide are presented in the imino form; but the process of the present invention is applicable to all of the isomeric forms of these compounds.

The reaction is carried out at temperatures in the range of from about 0° to about 175° C; preferably from about 20° C to about 100° C.; and more preferably from about 20° C to about 50° C.

The symmetrical triazine compounds are reacted as finely divided solids. A suitable particle size distribution range is, for example, from about 2 to about 300 microns. A preferred particle size distribution for the finely divided symmetrical triazine compounds is from about 10 to about 150 microns.

The reaction between dichlorine monoxide and the selected symmetrical triazine compounds is generally carried out using at least stoichiometric amounts of reactants. Preferably an excess of dichlorine monoxide of from about 1 to about 50 mole percent is employed.

Where less than stoichiometric amounts of $Cl_2O$ are used, a reaction product which is a mixture of trichloroisocyanuric acid and chlorosubstituted ammelides or ammelines is obtained.

Any suitable contact time between the gaseous mixture and the solid symmetrical triazine compound may be used such as from about 0.1 second to about 30 minutes or longer.

During the reaction, it may be desirable to agitate the symmetrical triazine compound by mechanical means or to employ a rotating reactor having means such as flights to cascade the reactant. In a preferred embodiment, the process is conducted in a fluidized bed reactor where the gaseous mixture can be used advantageously to fluidize the symmetrical triazine compound. The principles in practice of employing fluidized bed reactors are well known as described, for example, in the Chemical Engineers Handbook, edited by R. H. Perry and C. H. Chilton, 5th edition, McGraw-Hill, 1973, Section 20, pages 64–74.

Water is formed during the reaction of the dichlorine monoxide and the symmetrical triazine compounds as shown in equations (4) and (5) above. The by-product water formed may be removed by vaporizing the water through suitably controlling the reaction temperature and the gas flow rate through the reactor.

Gaseous nitrogen trichloride is also formed during the reaction and its build-up in the reaction mixture should be avoided as it can be explosively dangerous.

To avoid this build-up it is possible, for example, to dilute the $NCl_3$ gas with a diluent gas such as nitrogen.

In an additional embodiment, an excess of the gaseous mixture $Cl_2O$ and the diluent gas is fed to the reactor to remove nitrogen trichloride produced by sweeping it from the reactor. The gaseous mixture of $Cl_2O$ and $NCl_3$ is then conducted to a scrubber unit containing an aqueous solution of a basic compound which decomposes the $NCl_3$.

The trichloroisocyanuric acid produced by the process of the present invention is recovered as a dry or slightly moist product which can be used directly with no further processing required except, if desired, additional drying.

The process of the present invention is further illustrated by the following example. All percentages are by weight unless otherwise specified.

EXAMPLE 1

Finely ground ammeline having a particle size range of 50 to 75 microns (0.039 mole) was placed in a funnel reactor. Chlorine monoxide, generated by the reaction of solid HgO and gaseous chlorine, was diluted with nitrogen gas. The gaseous mixture, fed thru the stem of the funnel, passed upward through the ammeline. The solid reaction mixture was stirred periodically. The available chlorine content of the product was found to be 91.5%. Infrared analysis provided a spectrum which was identical to that of trichloroisocyanuric acid (theoretical available chlorine content 91.5%). During the reaction complete conversion of the ammeline to trichloroisocyanuric acid was accomplished.

EXAMPLE 2

The procedure of Example 1 was employed to react 0.039 mole finely ground ammelide (50 to 100 microns) with the $Cl_2O - N_2$ gaseous mixture over a period of several hours. The product, dried at 100° C for 15 minutes, had an available chlorine content of 87%. The infrared spectrum was indicative of trichloroisocyanuric acid.

What is claimed is:

1. A process for producing trichloroisocyanuric acid by the reaction of a solid symmetrical triazine compound selected from the group consisting of ammeline, chlorosubstituted ammeline, ammelide, chlorosubstituted ammelide, and mixtures thereof with a gaseous mixture of dichlorine monoxide and a diluent gas, said gaseous mixture being comprised of from about 1 percent to about 30 percent by volume of said dichlorine monoxide, and recovering said trichloroisocyanuric acid produced thereby.

2. The process of claim 1 in which said diluent gas is selected from the group consisting of air, nitrogen, carbon dioxode, chlorine, and nitrous oxide.

3. The process of claim 2 in which a reaction temperature of from about 20° to about 100° C is employed and said gaseous mixture contains from about 5 percent to about 25 percent by volume of dichlorine monoxide.

4. The process of claim 3 in which said solid symmetrical triazine compound has a particle size distribution range of from about 2 to about 300 microns.

5. The process of claim 4 in which said diluent gas is selected from the group consisting of air, chlorine and nitrogen.

6. The process of claim 5 in which said symmetrical triazine compound is selected from the group consisting of ammelide, chlorosubstituted ammelide and mixtures thereof.

7. The process of claim 5 in which said symmetrical triazine compound is selected from the group consisting of ammeline, chlorosubstituted ammeline, and mixtures thereof.

* * * * *